(12) United States Patent
Portal

(10) Patent No.: US 10,995,052 B2
(45) Date of Patent: *May 4, 2021

(54) BIAROMATIC PROPYNYL COMPOUNDS, PHARMACEUTICAL AND COSMETIC COMPOSITIONS CONTAINING SAME, AND USES THEREOF

(71) Applicant: GALDERMA RESEARCH & DEVELOPMENT, Biot (FR)

(72) Inventor: Thibaud Portal, Opio (FR)

(73) Assignee: Galderma Research & Development, Biot (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/075,592

(22) PCT Filed: Feb. 3, 2017

(86) PCT No.: PCT/IB2017/000075
§ 371 (c)(1),
(2) Date: Aug. 3, 2018

(87) PCT Pub. No.: WO2017/134513
PCT Pub. Date: Aug. 10, 2017

(65) Prior Publication Data
US 2019/0337881 A1 Nov. 7, 2019

Related U.S. Application Data

(60) Provisional application No. 62/290,707, filed on Feb. 3, 2016.

(51) Int. Cl.
| | | |
|---|---|---|
| *C07D 213/80* | (2006.01) | |
| *A61K 31/4406* | (2006.01) | |
| *C07C 65/19* | (2006.01) | |
| *A61K 8/368* | (2006.01) | |
| *A61Q 19/00* | (2006.01) | |
| *A61Q 19/08* | (2006.01) | |
| *A61K 8/49* | (2006.01) | |

(52) U.S. Cl.
CPC .............. *C07C 65/19* (2013.01); *A61K 8/368* (2013.01); *A61K 8/4926* (2013.01); *A61Q 19/00* (2013.01); *A61Q 19/08* (2013.01); *C07D 213/80* (2013.01); *C07C 2601/02* (2017.05); *C07C 2601/14* (2017.05); *C07C 2602/10* (2017.05)

(58) Field of Classification Search
CPC .. C07D 213/80; C07C 65/03; A61K 31/4406; A61K 31/192; A61K 8/36
USPC .................. 546/322; 562/473; 514/356, 569
See application file for complete search history.

(56) References Cited

U.S. PATENT DOCUMENTS

| | | | |
|---|---|---|---|
| 4,994,489 A * | 2/1991 | Wuest ................... | C07C 33/38 |
| | | | 514/510 |
| 5,149,705 A | 9/1992 | Chandraratna | |
| 5,498,795 A * | 3/1996 | Song ..................... | C07C 65/19 |
| | | | 544/238 |
| 5,776,699 A | 7/1998 | Klein et al. | |
| 6,046,220 A | 4/2000 | Bernardon | |
| 7,148,245 B2 | 12/2006 | Bernardon et al. | |
| 8,293,803 B2 * | 10/2012 | Przyborski .......... | A61K 31/216 |
| | | | 435/377 |
| 10,377,694 B2 * | 8/2019 | Portal ................... | A61Q 19/08 |
| 2001/0056105 A1 | 12/2001 | Bernardon et al. | |
| 2009/0036536 A1 | 2/2009 | Biadatti et al. | |

FOREIGN PATENT DOCUMENTS

| | | | |
|---|---|---|---|
| CA | 1335651 | 5/1995 | |
| EP | 0176034 | 4/1986 | |
| EP | 0253393 | 1/1988 | |
| EP | 0661258 | 7/1995 | |
| FR | 2746098 | 9/1997 | |
| FR | 2767525 | 2/1999 | |
| FR | 2767526 | 2/1999 | |
| FR | 2894960 | 6/2007 | |
| IL | 76454 A | 1/1989 | |
| IL | 111967 A | 6/2000 | |
| RU | 2329263 C2 | 7/2008 | |
| WO | WO-88/00466 A1 | 1/1988 | |
| WO | WO 99/02497 * | 1/1999 | ........... C07D 213/00 |
| WO | 99/10308 | 3/1999 | |

OTHER PUBLICATIONS

Kuzmanich, G. et al.: Photonic amplification by a single-state quantum reaction in the photodecarbonylation of crystalline diarylcyclopropenones. J. of the Am. Chem. Soc., vol. 131, pp. 11606-11614, 2009.*
Bollinger, J.L. et al.: Highly convenient, clean, fast and reliable sonogashira coupling reactions promoted by aminophosphine-based pincer complexes of palladium performed under addditive and amino-free conditions. Adv. Synth. & Catal., vol. 351, pp. 891-902, 2009.*
Auzias, M.G. et al.: 3-3'-bis(arylbenzofurans) via a gold-catalyzed domino process. Synlett, vol. 16. pp. 2443-2448, 2010.*
Leon, T. et al.: BF-3 mediated oxidative cross-coupling of pyridines with alkynyllithium reagents and further reductive functionalization of the pyridine scaffold. Synthesis, vol. 46, pp. 1374-1379, 2014.*
Novak, Z. et al.: The first total synthesis of Cicerfuran utilizing a one-pot synthesis of hydroxylated benzofurans. Tetrahedron, vol. 59, pp. 7509-7513, 2003.*
International Search Report and Written Opinion of the International Searching Authority dated Jul. 17, 2017 corresponding to International Patent Application No. PCT/IB2017/000075, 25 pages.

(Continued)

*Primary Examiner* — Charanjit Aulakh
(74) *Attorney, Agent, or Firm* — Clark & Elbing LLP

(57) ABSTRACT

Compounds of general formula (I) are described. Also described, is the use of such compounds in pharmaceutical compositions for use in human or veterinary medicine (dermatological, rheumatic, respiratory, cardiovascular and ophthalmologic disorders, in particular), or in cosmetic compositions.

19 Claims, No Drawings

(56) References Cited

OTHER PUBLICATIONS

Tamura, Koji et al., "Synthetic retinoids, retinobenzoic acids, Am80, Am580 and Ch55 regulate morphogenesis in chick limb bud", Cell Differentiation and Development, vol. 32, No. 1, pp. 17-26 (1990).
Office Action for Russian Patent Application No. 2018131460, dated Mar. 23, 2020 (17 pages).
Office Action for Israeli Patent Application No. 260967, dated Sep. 15, 2020 (17 pages).

* cited by examiner

BIAROMATIC PROPYNYL COMPOUNDS, PHARMACEUTICAL AND COSMETIC COMPOSITIONS CONTAINING SAME, AND USES THEREOF

CROSS-REFERENCE TO PRIOR APPLICATIONS

This application is the U.S. National Stage of PCT/IB2017/000075, filed Feb. 3, 2017, (published in the French language on Aug. 10, 2017 as WO 2017/134513 A1; the title and abstract were also published in English), which claims priority under 35 U.S.C. § 119 of U.S. Provisional Application No. 62/290,707, filed Feb. 3, 2016, each hereby expressly incorporated by reference in its entirety and each assigned to the assignee hereof.

The invention relates to bi-aromatic compounds as novel and useful industrial products. It also relates to the use of these novel compounds in pharmaceutical compositions intended for use in human or veterinary medicine, or in cosmetic compositions.

The compounds according to the invention have marked activity in the domains of cellular differentiation and proliferation, and find applications more particularly in the topical and systemic treatment of dermatological conditions related to a keratinization disorder, dermatological (or other) conditions with an inflammatory and/or immunoallergic component, and dermal or epidermal proliferations, whether benign or malignant. These compounds may also be used in the treatment of connective-tissue degeneration disorders, to combat skin aging, whether photo-induced or chronological, and to treat healing disorders. They can also be applied in the ophthalmological field, especially in the treatment of corneal diseases.

The compounds according to the invention can also be used in cosmetic compositions for body and hair hygiene.

The compounds according to the invention can be represented by general formula (I) below:

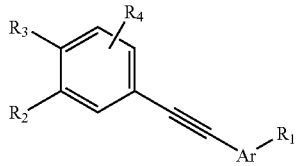

(I)

in which:

Ar represents a radical chosen from among the radicals of formulas (a) or (b) below:

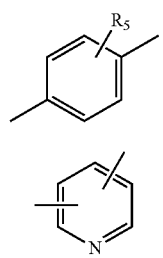

$R_5$ having the meaning given below, $R_1$ represents: (i) a hydrogen atom
(ii) a —$CH_3$ radical
(ii) a —$CH_2$—O—$R_6$ radical
(iv) an —O—$R_6$ radical
(v) a —CO—$R_7$ radical,
(vi) an —S(O)$_t$$R_9$ radical $R_6$, $R_7$, $R_9$ and t having the meaning given below, $R_2$ and $R_3$ represent a hydrogen atom, a linear or branched alkyl radical having 1 to 20 carbon atoms, an —O$R_6$ radical or an —S$R_6$ radical, $R_6$ having the meaning given below, given that $R_2$ and $R_3$, taken together, can form with the adjacent aromatic ring a 5- or 6-member ring optionally substituted by methyl groups and/or optionally interrupted by an oxygen or sulfur atom, $R_4$ represents a hydrogen atom, a halogen atom, a lower alkyl radical or an —O$R_6$ radical, $R_6$ having the meaning given below, given that in all of the preceding:

$R_6$ represents a hydrogen atom, a lower alkyl radical, a linear or branched alkyl radical having 1 to 20 carbon atoms, an —O—$CH_3$—$R_9$ radical or a —CO—$R_9$ radical, $R_9$ having the meaning given below, $R_7$ represents:
(a) a hydrogen atom
(b) a lower alkyl radical
(c) a radical of formula:

R' and R" having the meaning given below,
(d) an —O$R_8$ radical, $R_8$ having the meaning given below, $R_8$ represents a hydrogen atom, methyl, ethyl, propyl, cyclopropyl, cyclobutyl, or cyclopentyl, an alkenyl radical, a mono- or polyhydroxyalkyl radical, an optionally substituted aryl or aralkyl radical or a sugar residue or an amino acid or peptide residue, $R_9$ represents a lower alkyl or methyl, ethyl, propyl, cyclopropyl, cyclobutyl, cyclopentyl radical, R' and R" represent a hydrogen atom, a lower alkyl radical, a mono- or polyhydroxyalkyl radical, an optionally substituted aryl radical or an amino acid or peptide or sugar residue, or even, taken together, form a heterocycle, t is a whole number equal to 0, 1 or 2.

The invention also pertains to salts of compounds of formula (I) above in the case where $R_1$ represents a carboxylic acid function, as well as the optical and geometric isomers of said compounds. When compounds according to the invention are present in the form of salts, they are preferably alkali metal or alkaline-earth metal salts, or even zinc or an organic amine compound.

According to the present invention, lower alkyl radical means a radical having 1 to 6 carbon atoms, preferably methyl, ethyl, isopropyl, butyl, tert-butyl and hexyl radicals.

Linear or branched alkyl radical having 1 to 20 carbon atoms means, in particular, methyl, ethyl, propyl, cyclopropyl, cyclobutyl, cyclopentyl, 2-ethylhexyl, octyl, dodecyl, hexadecyl, and octadecyl radicals.

Monohydroxyalkyl radical means a radical preferably having 2 or 3 carbon atoms, notably a 2-hydroxyethyl, 2-hydroxypropyl, or 3-hydroxypropyl radical.

Polyhydroxyalkyl radical means a radical preferably containing 3 to 6 carbon atoms and 2 to 5 hydroxyl groups such as 2,3-dihydroxypropyl, 2,3,4-trihydroxybutyl, 2,3,4,5-tetrahydroxypentyl radicals or pentaerythritol residue.

Aryl radical means, preferably, a phenyl radical optionally substituted with at least one halogen atom, a hydroxyl, or a nitro function.

Aralkyl radical means, preferably, the benzyl or phenethyl radical optionally substituted with at least one halogen atom, hydroxyl, or a nitro function.

Alkenyl radical means a radical containing preferably 1 to 5 carbon atoms and having one or more ethylene unsaturations, such as, more particularly, the allyl radical.

Sugar residue means a residue particularly deriving from glucose, galactose or mannose, or even glucuronic acid.

Amino acid residue particularly means a residue deriving from lysine, glycine or aspartic acid, and peptide residue means, more particularly, a dipeptide or tripeptide residue resulting from the combination of amino acids.

Finally, heterocycle particularly means, preferably, a piperidino, morpholino, pyrrolidino or piperazino radical, possibly substituted in position 4 by a $C_1$-$C_6$ alkyl radical or mono- or polyhydroxyalkyl such as defined above.

When $R_4$ and $R_5$ represent a halogen atom, this is preferably a fluorine, chlorine or bromine atom.

The compounds of general formula (I) above within the scope of the present invention notably include the following compounds:

According to the present invention, the compounds of formula (I) more particularly preferred are those for which $R_5$ represents —OH, $R_7$ represents an $OR_8$ radical, and $R_{11}$ represents an —$OR_6$ radical, $R_6$ and $R_{11}$ having the meaning given above.

The compounds according to the invention are particularly well suited in the following treatment fields:

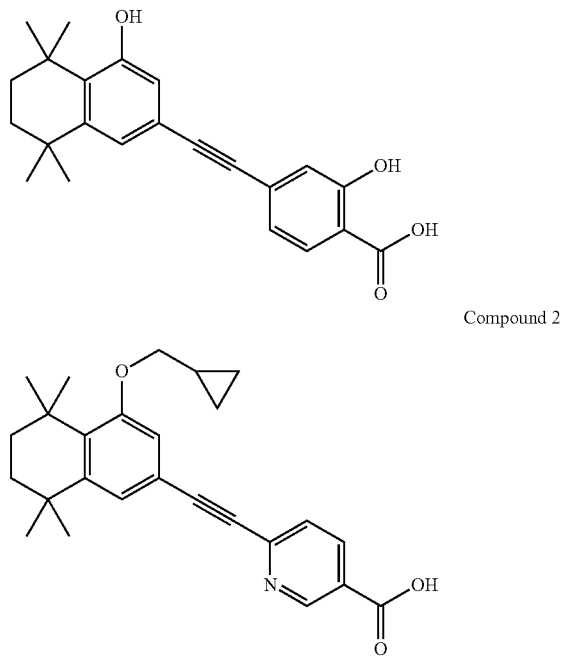

Compound 1

Compound 2

1) to treat dermatological conditions linked to a keratinization disorder pertaining to cellular differentiation and proliferation, especially to treat acne vulgaris, comedonic or polymorphic acne, rosacea, nodulocystic acne, acne conglobata, senile acne, and secondary *acnes* such as solar, drug-induced or occupational acne;
2) to treat keratinization disorders, especially ichthyosis, ichthyosiform states, Darier's disease, palmoplantar keratoderma, leukoplakia and leukoplakiform conditions, cutaneous or mucosal (buccal) lichen;
3) to treat other dermatological conditions associated with a keratinization disorder with an inflammatory and/or immunoallergic component and, in particular, all forms of psoriasis whether cutaneous, mucosal or nail, and psoriatic arthritis, or cutaneous atopy, such as eczema or respiratory atopy or gingival hypertrophy; the compounds may also be used in certain inflammatory conditions which do not present a keratinization disorder,
(4) to treat dermal or epidermal proliferations, whether benign or malignant, whether of viral origin or not such as common warts, flat warts and verruciform epidermodysplasia, oral or florid papillomatoses and proliferations that can be induced by UV radiation, in particular basal and prickle cell epithelioma,
5) to treat other dermatological disorders such as bullous dermatosis and collagen diseases,
6) to treat certain ophthalmological problems, especially corneal diseases,
7) to repair or combat aging of the skin, whether photo-induced or chronological or to reduce pigmentation and actinic keratosis, or any pathologies associated with chronological or actinic aging,
8) to prevent or treat *stigmata* of epidermal and/or dermal atrophy induced by local or systemic corticosteroids, or any other form of cutaneous atrophy,
9) to prevent or treat healing disorders or to prevent or repair stretch marks,
10) to combat disorders of sebaceous function, such as hyperseborrhea associated with acne or simple seborrhea,
11) in the treatment or prevention of cancerous or precancerous conditions,
12) in the treatment of inflammatory disorders such as arthritis,
13) in the treatment of any skin or general condition of viral origin,
14) in the prevention or treatment of alopecia,
15) in the treatment of dermatological or general conditions with an immunological component,
16) in the treatment of cardiovascular system disorders such as atherosclerosis.

In the abovementioned therapeutic fields, the compounds according to the invention can advantageously be used in combination with other compounds with retinoid activity, with D vitamins or derivatives thereof, with corticosteroids, with anti-free radicals, α-hydroxy or α-keto acids or derivatives thereof, or with ion channel blockers. D vitamins or derivatives thereof means, for example, vitamin $D_2$ or $D_3$ derivatives and in particular 1,25-dihydroxyvitamin $D_3$. Anti-free radicals means, for example, α-tocopherol, superoxide dismutase, ubiquinol or certain metal chelators. α-hydroxy or α-keto acids or derivatives thereof means, for example, lactic, malic, citric, glycolic, mandelic, tartaric, glyceric or ascorbic acids or salts thereof, amides or esters. Finally, ion channel blockers means, for example, minoxidil (2,4-diamino-6-piperidino-pyrimidine-3-oxide) and its derivatives.

The present invention also has for a subject medicinal compositions containing at least one compound of formula (I) such as defined above, one of its optical or geometric isomers or one of its salts.

The present invention therefore also has for a subject a novel medicinal composition intended in particular for treatment of the abovementioned conditions, which is characterized by the fact that it comprises, in a pharmaceutically-acceptable carrier and compatible with the selected mode of administration thereof, at least one compound of formula (I), one of the optical isomers thereof or one of the salts thereof.

The composition according to the invention can be administered enterally, parenterally, topically or ocularly.

For enteral administration, the composition may be in the form of tablets, hard capsules, dragées, syrups, suspensions, solutions, powders, granulates, emulsions, microspheres or nanospheres or lipid or polymer vesicles permitting controlled release. For parenteral administration, the compositions can advantageously be in the form of solutions or suspensions for infusion or for injection.

The compounds according to the invention are generally administered at a daily dosage of approximately 0.01 mg/kg to 100 mg/kg of bodyweight, in 1 to 3 doses.

For topical administration, the pharmaceutical compositions based on compounds according to the invention are more particularly intended for treatment of the skin and mucosa and may then be in the form of ointments, creams, milks, pomades, powders, swabs, solutions, gels, sprays, lotions or suspensions. They may also be in the form of microspheres or nanospheres or lipid or polymer vesicles, or polymer patches and hydrogels permitting controlled release. These topical compositions may also be in the anhydrous or the aqueous form, depending on the clinical indication.

For ocular administration, they are mainly eye drops.

These compositions for topical or ocular use contain at least one compound of formula (I) such as defined above, or one of the optical or geometric isomers thereof or one of the salts thereof, at a concentration preferably comprised between 0.001% and 5% by weight relative to the total weight of the composition.

Compounds of formula (I) according to the invention also find application in the cosmetic field, in particular in body and hair hygiene and especially for the treatment of acne-prone skin, for hair regrowth and loss prevention, to treat oily skin or hair, to protect against the harmful aspects of the sun or in the treatment of physiologically dry skin, to prevent and/or to combat photo-induced or chronological aging.

In the cosmetic field, the compounds according to the invention can further advantageously be used in combination with other compounds with retinoid activity, with D vitamins or derivatives thereof, with corticosteroids, with anti-free radicals, α-hydroxy or α-keto acids or derivatives thereof, or with ion channel blockers, all these various products being as defined above.

The present invention therefore also relates to a cosmetic composition which is characterized by the fact that it comprises, in a cosmetically-acceptable carrier and suitable for topical application, at least one compound of formula (I) as defined above or one of the optical or geometric isomers thereof or one of the salts thereof; this cosmetic composition may be in the form of a cream, a milk, a lotion, a gel, microspheres or nanospheres or lipid or polymer vesicles, a soap or a shampoo.

The concentration in compound of formula (I) in cosmetic compositions according to the invention is advantageously comprised between 0.001% and 3% by weight relative to the whole composition.

The medicinal and cosmetic compositions according to the invention may also contain inert additives or even pharmacodynamically or cosmetically-active additives, or combinations of these additives, and in particular: wetting agents; depigmenting agents such as hydroquinone, azelaic acid, caffeic acid or kojic acid; emollients; hydrating agents such as glycerol, PEG 400, thiamorpholinone, and derivatives thereof or urea; anti-seborrheic or anti-acne agents, such as S-carboxymethylcysteine, S-benzyl-cysteamine, salts or derivatives thereof, or benzoyl peroxide; antibiotics such as erythromycin and esters thereof, neomycin, clindamycin and esters thereof, tetracyclines; antifungal agents such as ketoconazole or polymethylene-4,5-isothiazolidones-3; agents promoting regrowth of hair such as minoxidil (2,4-diamino-6-piperidino-pyrimidine-3-oxide) and derivatives thereof, diazoxide (7-chloro-3-methyl-1,2,4-benzothiadiazine 1,1-dioxide) and phenytoin (5,4-diphenyl-imidazolidine 2,4-dione); non-steroidal anti-inflammatory agents; carotenoids and, in particular, β-carotene; anti-psoriatic agents such as anthralin and derivatives thereof; and finally eicosa-5,8,11,14-tetraynoic and eicosa-5,8,11-trynoic acids, esters and amides thereof.

The compositions according to the invention may also contain flavors, preservatives such as para-hydroxybenzoic acid esters, stabilizers, moisture regulators, pH regulators, osmotic pressure modifiers, emulsifiers, UV-A and UV-B filters, antioxidants such as α-tocopherol, butylhydroxyanisole or butylhydroxytoluene.

We will now give several examples, for illustration purposes and non-limiting, to validate the activity of active compounds of formula (I) according to the invention, as well as various concrete formulations based on such compounds.

EXAMPLE 1: TRANSACTIVATION TEST a) Test Principle:

Activation of receptors by an agonist (activator) in HeLa cells leads to the expression of a reporter gene, luciferase, which generates light in the presence of a substrate. Therefore the activation of receptors can be measured by quantifying the luminescence produced after incubation of the cells in the presence of a reference antagonist. The activator products displace the antagonist from its site, thus permitting the receptor to be activated. The activity is measured by quantifying the increase in light produced. This measurement determines the activating activity of the useful compound in the invention.

In this study, a constant is determined that represents the affinity of the molecule for the receptor. This value can fluctuate according to the basal activity and expression of the receptor; it is designated apparent Kd (KdApp).

To determine this constant, cross curves are created of the product to be tested (4'-(3-hydroxy-propyl)-3'-(5,5,8,8-tetramethyl-5,6,7,8-tetrahydro-naphthalen-2-yl)-biphenyl-4-carboxylic acid and 4'-(2,3-dihydroxy-propyl)-3'-(5,5,8,8-tetramethyl-5,6,7,8-tetrahydro-naphtalen-2-yl)-biphenyl-4-carboxylic) acid versus a reference antagonist also called reference ligand, 4-(5,5-dimethyl-8-p-tolyl-5,6-dihydro-naphthalen-2-ylethynyl)-benzoc acid. The product to be tested is used at 10 concentrations and the reference antagonist at 7 concentrations. In each well (of a 96-well plate), the cells are in contact with one concentration of the product to be tested and one concentration of the reference antagonist.

Full agonist controls, also called 100% controls, (4-[2-(5, 5,8,8 tetramethyl-5,6,7,8 tetrahydronaphthalene-2-yl)propenyl]-benzoic acid) and inverse agonist controls, also called 0% controls, (4-{(E)-3-[4-(4-tert-butyl-phenyl)-5,5,8,8-tetramethyl-5,6,7,8-tetrahydro-naphthalen-2-yl]-3-oxo-propenyl}-benzoic acid) are also measured.

These cross curves allow determining the AC50 (concentration at which 50% activation of the receptor is observed) of the reference ligand at different concentrations of the product to be tested. These AC50s are used to calculate the Schild regression by plotting a line conforming to the Schild equation ("Quantitation in receptor pharmacology" Terry P. Kenakin, Receptors and Channels, 2001, 7, 371-385).

In the case of an agonist, the AC50 is calculated by plotting the curve of the product at the concentration of the reference ligand giving 80% activation. The percentage of activation that corresponds to the maximum level of activity obtained is also measured.

b) Materials and Method:

The HeLa cell lines used are stable transfectants containing the plasmids ERE-βGlob-Luc-SV-Neo (reporter gene) and RAR (α, β, γ) ER-DBD-puro. These cells are inoculated onto 96-well plates in an amount of 10,000 cells per well in 100 µl DMEM medium with no phenol red and supplemented with 10% delipidated fetal bovine serum. The plates are then incubated at 37° C., 7% $CO_2$ for 4 hours.

The different dilutions of the product to be tested, the reference ligand (4-(5,5-dimethyl-8-p-tolyl-5,6-dihydro-naphthalen-2-ylethynyl)-benzoic acid), the 100% control (100 nM 4-[2-(5,5,8,8 tetramethyl-5,6,7,8 tetrahydronaphthalene-2-yl)propenyl]-benzoic acid) and the 0% control (500 nM 4-{(E)-3-[4-(4-tert-butyl-phenyl)-5,5,8,8-tetramethyl-5,6,7,8-tetrahydro-naphthalen-2-yl]-3-oxo-propenyl}-benzoic acid) are added in an amount of 5 µl per well. The plates are then incubated 18 hours at 37° C., 7% $CO_2$.

The culture medium is removed by turning over and 100 µl of a 1:1 PBS (phosphate buffer solution)/luciferin mixture is added to each well. After 5 minutes, the plates are read by the luminescence reader.

c) Results:

The apparent Kd constant values are indicated in the table below. These values are compared to those of the compounds of patent WO 99/10308 presenting the best activities

|  | RAR alpha Kdapp (nM) | RAR beta Kdapp (nM) | RAR gamma Kdapp (nM) |
|---|---|---|---|
| Compound 1 | 120 | 4 | 4 |
| Compound 2 | 30 | 2 | 4 |

EXAMPLE 2

In this example, various concrete formulations based on the compound according to the invention are illustrated.

A—Oral Administration (a) 0.2 g tablet

| Compound prepared in Example 7 | 0.001 g |
|---|---|
| Starch | 0.114 g |
| Dicalcium phosphate | 0.020 g |
| Silica | 0.020 g |
| Lactose | 0.030 g |
| Talc | 0.010 g |
| Magnesium stearate | 0.005 g |

(b) Oral suspension in 5-ml ampoules

| Compound prepared in Example 3 | 0.001 g |
|---|---|
| Glycerin | 0.500 g |
| 70% sorbitol | 0.500 g |
| Sodium saccharin | 0.010 g |
| Methyl parahydroxybenzoate | 0.040 g |
| Flavor | qs |
| Purified water | qs 5 ml |

(c) 0.8 g tablet

| Compound of Example 6 | 0.500 g |
|---|---|
| Pregelatinized starch | 0.100 g |
| Microcrystalline cellulose | 0.115 g |
| Lactose | 0.075 g |
| Magnesium stearate | 0.010 g |

(d) Oral suspension in 10-ml ampoules

| Compound of Example 2 | 0.200 g |
|---|---|
| Glycerin | 1.000 g |
| 70% sorbitol | 1.000 g |
| Sodium saccharin | 0.010 g |
| Methyl parahydroxybenzoate | 0.080 g |
| Flavor | qs |
| Purified water | qs 10 ml |

B—Topical Administration (a) Ointment

| Compound of Example 9 | 0.020 g |
|---|---|
| Isopropyl myristate | 81.700 g |
| Liquid Vaseline oil | 9.100 g |
| Silica ("Aerosil 200" sold by DEGUSSA) | 9.180 g |

(b) Ointment

| Compound of Example 10 | 0.300 g |
|---|---|
| Codex white Vaseline | 100 g |

(c) Nonionic water-in-oil cream

| 2-hydroxy-4-[3-hydroxy-3-(3-tert-butyl-4-hydroxyphenyl)]-1-propynylbenzoic acid | 0.100 g |
|---|---|
| Mixture of emulsive lanolin alcohols, waxes and oils (anhydrous Eucerin) sold by BDF) | 39.900 g |
| Methyl parahydroxybenzoate | 0.075 g |
| Propyl parahydroxybenzoate | 0.075 g |
| Sterile demineralized water: qs | 100 g |

(d) Lotion

| Compound of Example 8 | 0.100 g |
|---|---|
| Polyethylene glycol (PEG 400) | 69.900 g |
| Ethanol (95%) | 30.000 g |

(e) Hydrophobic ointment

| Compound of Example 7 | 0.300 g |
|---|---|
| Isopropyl myristate | 36.400 g |
| Silicone oil ("Rhodorsil 47 V 300" sold by RHONE-POULENC) | 36.400 g |
| Beeswax | 13.600 g |
| Silicone oil ("Abil 300.000 cst" sold by GOLDSCHMIDT) | 100 g |

(f) Nonionic oil-in-water cream

| Compound of Example 3 | 1.000 g |
|---|---|
| Cetyl alcohol | 4.000 g |
| Glycerol monostearate | 2.500 g |
| PEG 50 stearate | 2.500 g |
| Shea butter | 9.200 g |
| Propylene glycol | 2.000 g |
| Methyl parahydroxybenzoate | 0.075 g |
| Propyl parahydroxybenzoate | 0.075 g |
| Sterile demineralized water: | 100 g |

The invention claimed is:

1. A compound having the structure of formula (I) below:

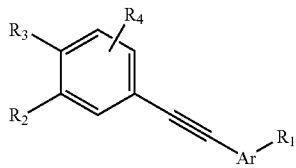

(I)

in which:

Ar is a radical selected from the group of radicals of formula (a) or (b) below:

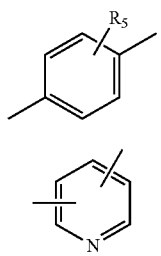

wherein $R_5$ is OH;

$R_1$ is: (i) a hydrogen atom,
(ii) a —$CH_3$ radical,
(ii) a —$CH_2$—O—$R_6$ radical,
(iv) an —O—$R_6$ radical,
(v) a —CO—$R_7$ radical, or
(vi) an —S(O)$_t R_9$ radical;

$R_2$ and $R_3$, together with the carbon atoms to which they are attached, form a 5- or 6-membered ring optionally substituted by methyl groups and includes only carbon atoms;

$R_4$ is a halogen atom or an —O$R_6$ radical;

$R_6$ is a hydrogen atom, a lower alkyl radical, a linear or branched alkyl radical having 1 to 20 carbon atoms, or a —CO—$R_9$ radical;

$R_7$ is a hydrogen atom, a lower alkyl radical, a radical of formula:

or
an —O$R_8$ radical;

$R_8$ is a hydrogen atom, a linear or branched alkyl radical having 1 to 20 carbon atoms, an alkenyl radical, a mono- or polyhydroxyalkyl radical, an optionally substituted aryl or aralkyl radical, a sugar residue, an amino acid, or a peptide residue;

$R_9$ represents a lower alkyl radical, or a linear or branched alkyl radical having 1 to 20 carbon atoms;

each of R' and R" is a hydrogen atom, a lower alkyl radical, a mono- or polyhydroxyalkyl radical, an optionally substituted aryl radical, an amino acid, a peptide residue, or a sugar residue; or R' and R", together with the nitrogen atom to which they are attached, form a heterocycle; and t is 0, 1 or 2, or a salt, or an optical or geometric isomer thereof.

2. The compound according to claim 1, wherein the compound is an alkali metal or alkaline earth metal salt, a zinc salt, or an organic amine salt.

3. The compound according to claim 1, wherein the lower alkyl radicals are selected from the group consisting of methyl, ethyl, isopropyl, butyl, tert-butyl, and hexyl radicals.

4. The compound according to claim 1, wherein the linear or branched alkyl radicals having 1 to 20 carbon atoms are selected from the group consisting of methyl, ethyl, propyl, cyclopropyl, cyclobutyl, and cyclopentyl radicals.

5. The compound according to claim 1, wherein the monohydroxyalkyl radicals are selected from the group consisting of 2-hydroxyethyl, 2-hydroxypropyl, and 3-hydroxypropyl radicals.

6. The compound according to claim 1, wherein the polyhydroxyalkyl radicals are selected from the group consisting of 2,3-dihydroxypropyl, 2,3,4-trihydroxybutyl, 2,3,4,5-tetrahydroxypentyl radicals, and a pentaerythritol residue.

7. The compound according to claim 1, wherein the aryl radical is a phenyl radical optionally substituted with at least one halogen atom, hydroxyl, or nitro.

8. The compound according to claim 1, wherein the aralkyl radicals are selected from the group consisting of benzyl or phenethyl radicals optionally substituted by at least one halogen atom, hydroxyl, or nitro.

9. The compound according to claim 1, wherein the alkenyl radicals are selected from the group consisting of radicals containing 2 to 5 carbon atoms and having one or more double bonds.

10. The compound according to claim 1, wherein the sugar residues are selected from the group consisting of glucose, galactose, mannose, and glucuronic acid residues.

11. The compound according to claim 1, wherein the amino acid residues are selected from the group consisting of residues deriving from lysine, glycine, and aspartic acid.

12. The compound according to claim 1, wherein the peptide residues are selected from the group consisting of dipeptide and tripeptide residues.

13. The compound according to claim 1, wherein the heterocyclic radicals are selected from the group consisting of piperidino, morpholino, pyrrolidino, and piperazino radicals, optionally substituted in position 4 by a C1-C6 alkyl or mono- or polyhydroxyalkyl radical.

14. The compound according to claim 1, wherein the halogen atoms are selected from the group consisting of fluorine, chlorine, and bromine.

15. The compound according to claim 1, wherein the compound is an alkali metal salt, an alkaline earth metal salt, a zinc salt, or an organic amine salt of compound 1 or 2:

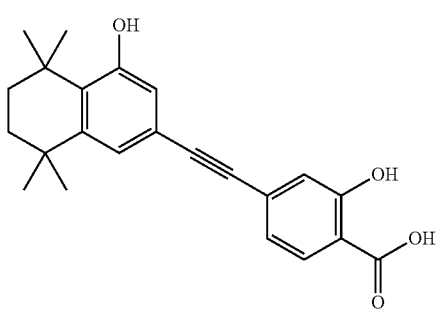

Compound 1

-continued

Compound 2

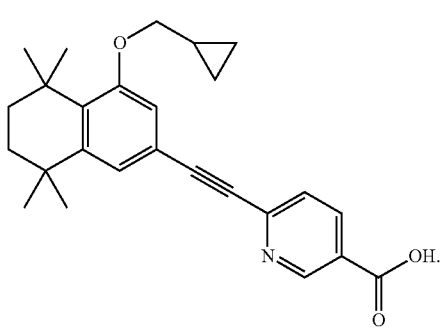

16. The compound according to claim 1, wherein $R_4$ is an $-OR_6$ radical, $R_1$ is a $-CO-R_7$ radical, and $R_7$ is an $-OR_8$ radical.

17. The compound according to claim 1, wherein the compound is added to a medicament.

18. The compound according to claim 9, wherein the alkenyl radical is an allyl radical.

19. A pharmaceutical or cosmetic composition comprising an effective amount of the compound of claim 1.

* * * * *